United States Patent [19]

Kleiner

[11] Patent Number: 4,670,191
[45] Date of Patent: Jun. 2, 1987

[54] PROCESS FOR THE PREPARATION OF N-PHOSPHONOMETHYLGLYCINE

[75] Inventor: Hans-Jerg Kleiner, Kronberg, Fed. Rep. of Germany

[73] Assignee: Hoechst Aktiengesellschaft, Frankfurt am Main, Fed. Rep. of Germany

[21] Appl. No.: 905,633

[22] Filed: Sep. 9, 1986

[30] Foreign Application Priority Data

Sep. 11, 1985 [DE] Fed. Rep. of Germany ....... 3532344

[51] Int. Cl.$^4$ .............................................. C07F 9/38
[52] U.S. Cl. ............................. 260/502.5 F; 423/437
[58] Field of Search ................................. 260/502.5 F

[56] References Cited

U.S. PATENT DOCUMENTS

| | | | |
|---|---|---|---|
| 3,799,758 | 3/1974 | Franz | 71/86 |
| 4,094,928 | 6/1978 | Gaertner | 260/502.5 F |
| 4,369,142 | 1/1983 | Moser | 260/502.5 F |
| 4,486,358 | 12/1984 | Moser | 260/502.5 F |

FOREIGN PATENT DOCUMENTS 0081459  6/1983  European Pat. Off. .

OTHER PUBLICATIONS

Wagner et al, "Synthetic Organic Chemistry" (1953), pp. 660 and 661.

*Primary Examiner*—J. E. Evans
*Attorney, Agent, or Firm*—Curtis, Morris & Safford

[57] ABSTRACT

A process for the preparation of N-phosphonomethylglycine by reaction of aminomethanephosphonic acid and glyoxylic acid in the molar ratio 1:2 in aqueous medium.

5 Claims, No Drawings

PROCESS FOR THE PREPARATION OF N-PHOSPHONOMETHYLGLYCINE

The present invention relates to a new process for the preparation of N-phosphonomethylglycine of the formula I

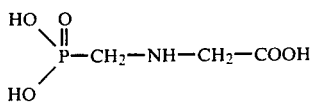   (I)

N-phosphonomethylglycine, whose preparation and use is described in U.S. Pat. No. 3,799,758, is a total herbicide having a very broad scope of application.

The preparation processes which have become known hitherto are, as a rule, based on reactions using formaldehyde in the presence of chlorine ions. The formation of cancerogenic bischloromethyl ether cannot be avoided in this case. In addition, N,N-bis-phosphonomethylglycine of the formula II

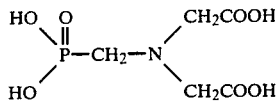   (II)

is frequently produced as a by-product.

In European Published Specification No. 0,081,459, it is proposed that aminomethanephosphonic acid be reacted with glyoxal in aqueous medium in the presence of sulfur dioxide. In this case, I is produced in yields of up to about 75%. but, besides this, II is produced as a by-product in considerable amounts. A further disadvantage of this process is the use of sulfur dioxide.

Finally, it is known from U.S. Pat. No. 4,094,928 that aminomethanephosphonic acid (ester) can be reacted with glyoxylic acid (ester) in an organic medium. In this case, the Schiff base of the formula

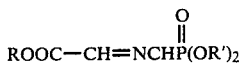   (III)

is produced, with elimination of water, which can be converted to I by reduction and, if appropriate, saponification. This process is disadvantageous since it requires several reaction stages and is associated with corresponding losses in yield.

It has now been found that the disadvantages of the known processes are avoided and N-phosphonomethylglycine is obtained in high yield and purity when aminomethanephosphonic acid of the formula IV

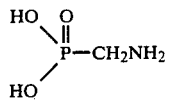   (IV)

or salts thereof with strong bases, is reacted with approximately double the molar amount of glyoxylic acid in an aqueous or water-containing medium.

Condensation with elimination of water and formation of the Schiff base does not occur under the conditions mentioned; instead, compound I is produced directly in a reaction sequence which is as yet unexplained; $CO_2$ is produced as a by-product.

The reaction occurs, for example, by presenting glyoxylic acid as a concentrated (50% strength) aqueous solution and adding IV in solid form in portions or as an aqueous solution; however, the reverse sequence can also be used.

A molar ratio of 1 part of IV and 2 parts of glyoxylic acid is preferably used, but one or other part can also be used in excess. The reaction is carried out at temperatures of 10°–100° C., preferably 30°–100° C.

In place of the free acid IV, its salts with strong bases can also be used, for example the alkali metal salts ($Na^+$, $K^+$), the ammonium salt or an amine salt, for example the ethylamine, triethylamine, isopropylamine or ethanolamine salt.

The reaction is heralded by a vigorous evolution of gas, which increases with rising temperature. After this evolution of gas has finished, the reaction mixture is cooled and the precipitated reaction product is isolated. For better separation of the latter, it can be of advantage to add a water-miscible organic solvent, such as acetone, acetonitril or methanol, to the reaction batch. The process can also be carried out continuously.

The reaction product I is produced in a yield of at least 70% and is virtually free of by-products.

The examples below serve to describe the present invention in more detail.

EXAMPLE 1

29.6 g (0.2 mol) of 50% strength aqueous glyoxylic acid solution were warmed to 40° C. with stirring. 11.1 g (0.1 mol) of aminomethanephosphonic acid were then added in portions at 40°–45° C., whereupon a vigorous evolution of gas commenced. After completion of the addition, the temperature was increased to an internal temperature of 85° C. After about 1 h, the evolution of gas was complete. The mixture was stirred for a further 15 min at 85° C., a little water was added, and the mixture was cooled. 10 g of N-phosphonomethylglycine, m.p.: 321°–323° C. [decomp.], were obtained. After concentration of the mother liquor and digestion of the precipitated crystal slurry using methanol/water, a further 2.5 g were obtained. The total yield was thus 74% of theory.

EXAMPLE 2

30 g (0.203 mol) of 50% strength aqueous glyoxylic acid solution were warmed to 40° C. with stirring, and a warm solution, at 40°–50° C., of 11.1 g (0.1 mol) of aminomethanephosphonic acid in 60 ml of water was added dropwise, whereupon evolution of gas commenced. The temperature was increased to 60° C. during the dropwise addition. After completion of the dropwise addition, the mixture was stirred for a further 1 h, the temperature being increased little by little to 100° C. After the gas evolution had finished, the mixture was stirred for a further 30 min at 100° C. and then cooled. 10.5 g of N-phosphonomethylglycine crystallized out during this. A further 2.5 g were obtained from the concentrated mother liquor. The total yield was thus 77% of theory.

EXAMPLE 3

29.6 g (0.2 mol) of 50% strength aqueous glyoxylic acid solution were warmed to 60° C. and 13.3 g (0.1 mol) of the Na salt of aminimethanephosphonic acid in 27 ml of water were added dropwise at 60° C. from a heatable dropping funnel within 2 h with stirring. The temperature was then raised slowly to 100° C. and the mixture was stirred for a further 10 min until evolution of gas no longer occurred. After cooling, the water was removed by distillation in vacuum, the residue remaining was digested using 30 g of concentrated hydrochloric acid, and the sodium chloride formed was filtered off under suction. The filtrate was concentrated in vacuo at about 50° C. The residue remaining was dried over KOH, digested using aqueous methanol (approx. 50% strength), shaken and filtered under suction, then washed with methanol and dried. 12 g of N-phosphonomethylglycine, yield 71% of theory, were obtained.

I claim:

1. A process for the preparation of N-phosphonomethylglycine of the formula

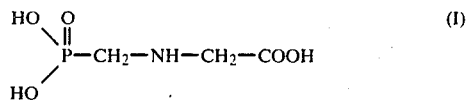

wherein aminomethanephosphonic acid of the formula

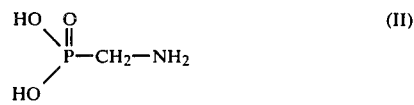

or salts thereof with strong bases, are reacted with glyoxylic acid in the molar ratio of about 1:2 in aqueous or aqueous-organic medium.

2. The process as claimed in claim 1, wherein the reaction is carried out at temperatures of 10°–100° C.

3. The process as claimed in claim 1, wherein a water-miscible organic solvent is added.

4. The process as claimed in claim 2, wherein the temperatures are 30° to 100° C.

5. The process as claimed in claim 3, wherein the solvent is acetone, acetonitril or methanol.

* * * * *